United States Patent [19]

Li

[11] Patent Number: 5,326,350
[45] Date of Patent: Jul. 5, 1994

[54] SOFT TISSUE CLOSURE SYSTEMS

[76] Inventor: Shu-Tung Li, 1 Kiowa Ter., Oakland, N.J. 07436

[21] Appl. No.: 881,213

[22] Filed: May 11, 1992

[51] Int. Cl.⁵ .......................... A61F 2/02; A61F 13/20
[52] U.S. Cl. ................................. 623/11; 128/DIG. 8; 604/15; 604/21; 604/208; 604/228; 604/117
[58] Field of Search ................... 128/DIG. 8; 604/15, 604/21, 208, 228, 117; 623/11

[56] References Cited

U.S. PATENT DOCUMENTS

| | | | |
|---|---|---|---|
| 3,157,524 | 11/1964 | Artandi | 106/122 |
| 3,364,200 | 1/1968 | Ashton et al. | 260/212 |
| 3,520,402 | 7/1970 | Nichols | 206/59 |
| 3,742,955 | 7/1973 | Battista et al. | 128/334 |
| 4,016,877 | 4/1977 | Cruz, Jr. et al. | 128/156 |
| 4,066,083 | 1/1978 | Ries | 128/325 |
| 4,215,200 | 7/1980 | Miyata et al. | 435/273 |
| 4,271,070 | 6/1981 | Miyata et al. | 260/123 |
| 4,412,947 | 11/1983 | Cioca | 260/123 |
| 4,515,637 | 5/1985 | Cioca | 424/94 |
| 4,578,067 | 3/1986 | Cruz, Jr. | 604/368 |
| 4,744,364 | 5/1988 | Kersey . | |
| 4,891,359 | 1/1990 | Saferstein et al. | 514/21 |
| 4,970,298 | 11/1990 | Silver et al. | 128/DIG. 8 |
| 5,141,496 | 8/1992 | Dalto et al. | 604/117 |

FOREIGN PATENT DOCUMENTS 2265416 10/1975 France ...................... 604/15

Primary Examiner—David Isabella
Assistant Examiner—Debra S. Brittingham

[57] ABSTRACT

A soft tissue closure system for closing a percutaneous puncture site or soft tissue voids, its method of manufacture and method of use are disclosed. The system comprises a delivery means and a self-expandable, resorbable implant disposed within the delivery means in a compressed configuration. Upon release of the implant member from the system within a soft tissue void, the implant member self-expands to conform to the shape of the soft tissue void and seals the void.

12 Claims, 3 Drawing Sheets

SOFT TISSUE CLOSURE SYSTEMS

FIELD OF INVENTION

This invention relates generally to the closure of soft tissue sites with self-expandable, bioresorbable, polymer implants, particularly to the closure of percutaneous puncture sites. The present invention is also directed to the delivery of such implants with tubular delivery devices which penetrate the soft tissue sites to a defined depth for hemostasis and wound closure. Methods of preparing the implants are also disclosed.

BACKGROUND OF THE INVENTION

It has been a routine practice to insert a catheter through a puncture site into a blood vessel to either treat a diseased blood vessel by a procedure known in the art as percutaneous transluminal angioplasty (PTA), or to deliver systemic drugs to the blood stream for chemotherapeutic applications. In the case of a PTA procedure, an introducer sheath is inserted into an artery through the puncture site such that a balloon or other type of catheter can then be inserted into the vessel to carry out the procedure within the vessel. Depending upon the nature of the disease and the site of arterial insertion, the size of an introducer sheath can vary from about 1 mm to as large as about 5 mm. One of the complications of these procedures is hemorrhaging at the percutaneous puncture site after removal of the catheter and the introducer sheath. In order to stop the bleeding, pressure is applied at the puncture site until hemostasis occurs. Since the angioplasty procedures often require the use of anticoagulant, the pressure approach is not always effective and may require a long period of pressurization.

A variety of commercial hemostatic products are available such as those disclosed in U.S. Pat. Nos. 2,465,357; 3,742,955; and 3,364,200. A felt or fleece like collagen hemostat is disclosed in U.S. Pat. No. 4,066,083. A hemostatic collagen paste comprising a mixture of collagen powder and saline is disclosed in U.S. Pat. No. 4,891,359. A number of other collagen based hemostatic materials are disclosed in U.S. Pat. Nos. 4,412,947; 4,578,067; 4,515,637; 4,271,070; 4,891,359; 4,066,083; 4,016,877 and 4,215,200. None of these patents teach the art of hemostasis at a vessel puncture site.

A device to close an arterial puncture site of a blood vessel is disclosed in U.S. Pat. No. 4,744,364 to Kensey. This device involves the insertion of an expandable, resorbable material inside of the lumen of a blood vessel via a tubular member which fits inside an introducer sheath. A retraction filament is secured to the resorbable material for pulling it to the puncture site so that the resorbable material engages the inner surface of the blood vessel contiguous with the puncture. The filament is held taut and taped or otherwise secured to patients, skin to hold the resorbable material in position.

The Kensey device introduces several potential risks to the patient. The device may induce an acute thrombosis due to imperfect alignment of the sealing material or to non-hemocompatibility of the material. The premature degradation of the filament may leave the sealing material unsecured, leading to embolization distal to the puncture site. The migration of the sealing material may not only cause rebleeding, but potential thrombosis which requires surgical intervention. The potential risks involved in such a device may outweigh the benefits such a device can offer. Thus, a safe and effective method to close a puncture site and stop the bleeding is still highly desirable and welcome.

Accordingly, it is the primary object of the present invention to provide an implant which will close a puncture site and stop the bleeding while substantially reducing the disadvantages and risks associated with the prior art.

It is a further object of the present invention to provide an implant which self-expands in vivo to fill the voids or defects of a tissue or organ with a biocompatible, resorbable material.

It is still a further object of the present invention to provide a method to deliver the biocompatible, resorbable implant material to tissues or organs of interest by a tubular delivery device.

It is another object of the present invention to provide a means to deliver medicaments, antibiotics, growth factors and other biologically active molecules to selected tissues or organs.

It is yet another object of the present invention to provide a method of manufacturing the implant.

SUMMARY OF THE INVENTION

By means of the present invention, a self-expandable, resorbable, hemostatic implant has been discovered which eliminates or substantially reduces many of the disadvantages and problems associated with the prior art attempts at closing the punctured wound sites in vessel catheterization and other soft tissue repair procedures. In addition, by means of the present invention, a method is provided to deliver medicaments to the selected site of a soft tissue. More specifically, by means of the present invention, a resorbable, self-expandable, hemostatic implant is delivered to a specific vessel puncture site to stop the bleeding in post angioplasty procedures.

The resorbable, self-expandable tissue closure implant of the present invention is generally a dry, porous matrix comprised of biological fibers. As used herein "biological fibers" include collagen, elastin, fibrin and polysaccharides. In a preferred form of the invention, the matrix is comprised of collagen fibers of animals or humans.

In particular, the self-expandable resorbable implant of the present invention comprises a matrix having pores with an average dimension of from about 100 um to about 3000 um in its fully expanded configuration.

The matrix may also include selected medicaments for local therapeutic applications. Therapeutic medicaments include, but are not limited to, hemostatic agents such as thrombin, $Ca^{++}$ and the like, wound healing agents such as epidermal growth factor (EGF), acidic and basic fibroblast growth factors (FGFs), transforming growth factors alpha and beta (TGF alpha and beta) and the like, glycoproteins such as laminin, fibronectin and the like, various types of collagens.

The method for fabricating the resorbable, self-expandable soft tissue closure implant, in its broadest embodiment, comprises:

a) forming an aqueous dispersion containing biological fibers;

b) pouring the aqueous dispersion into molds;

c) freeze-drying the aqueous dispersion;

d) crosslinking the freeze-dried matrix by treatment with crosslinking agent;

e) spraying the crosslinked matrix with water mist; and then f) compressing the water mist treated matrix.

Still further, the invention includes a method for closing a soft tissue puncture site with the resorbable, self-expandable implant. The method comprises delivering the resorbable, self-expandable polymer implant in its compressed configuration to the selected site by a delivery means, particularly a tubular delivery device, and releasing the resorbable implant at the selected soft tissue site where the resorbable implant self-expands to conform to the soft tissue site to close the defect. In particular, the method comprises:

a) inserting a delivery means into the void of the soft tissue to a depth controlled by a depth insertion guide provided on said delivery means;

b) ejecting a compressed implant from said delivery means into the void, said implant formed of a material capable of being resorbed in the living being having an average pore size in the range of from about 100 um to about 3,000 um and being self-expandable when wetted, forming an expanded, hydrated matrix conforming to the shape of and sealing the soft tissue void; and then c) removing the delivery means.

The invention also includes a device for sealing a void in a soft tissue of a living being comprising:

a) an implant formed of a material capable of being resorbed in the living being having an average pore size in the range of from about 100 um to about 3,000 um and being self-expandable when wetted;

b) a delivery means having an outlet at its distal end and a depth insertion guide, said delivery means being adapted to be inserted into the void to a depth which is controlled by the depth insertion guide, said implant being disposed within said delivery means in a compressed configuration; and c) an ejection means causing the compressed implant to pass out of said outlet into the void of the soft tissue to form an expanded, hydrated matrix which conforms to and seals the soft tissue void.

The resorbable self-expandable, soft tissue closure implant of the present invention is constructed such that the matrix is highly porous to provide maximal volume capacity and expansion, and surface area for fluid absorption, platelet adhesion and hemostasis. The highly porous matrix also provides maximal surface area for cell infiltration and adhesion for wound healing. Thus, in a preferred embodiment of the present invention, the self-expandable implant of the present invention has the following physical characteristics and physico-chemical properties.

| Physical Characteristics: | |
| --- | --- |
| Diameter of the cylinder (cm) | 1–10 |
| Height of the cylinder (cm) | 0.2–5 |
| Pore size (um) | 100–3000 |
| Density (g/cm$^3$) | 0.02–0.50 |
| Physico-chemical Properties: | |
| Swelling Capacity (g/g) | 2–70 |
| Thermal Shrinkage (°C.) | 50–75 |
| Relaxation Recovery Time (seconds) | 1–30 |

The invention will next be described in connection with certain illustrated embodiments.

DESCRIPTION OF THE INVENTION

Figure 1:
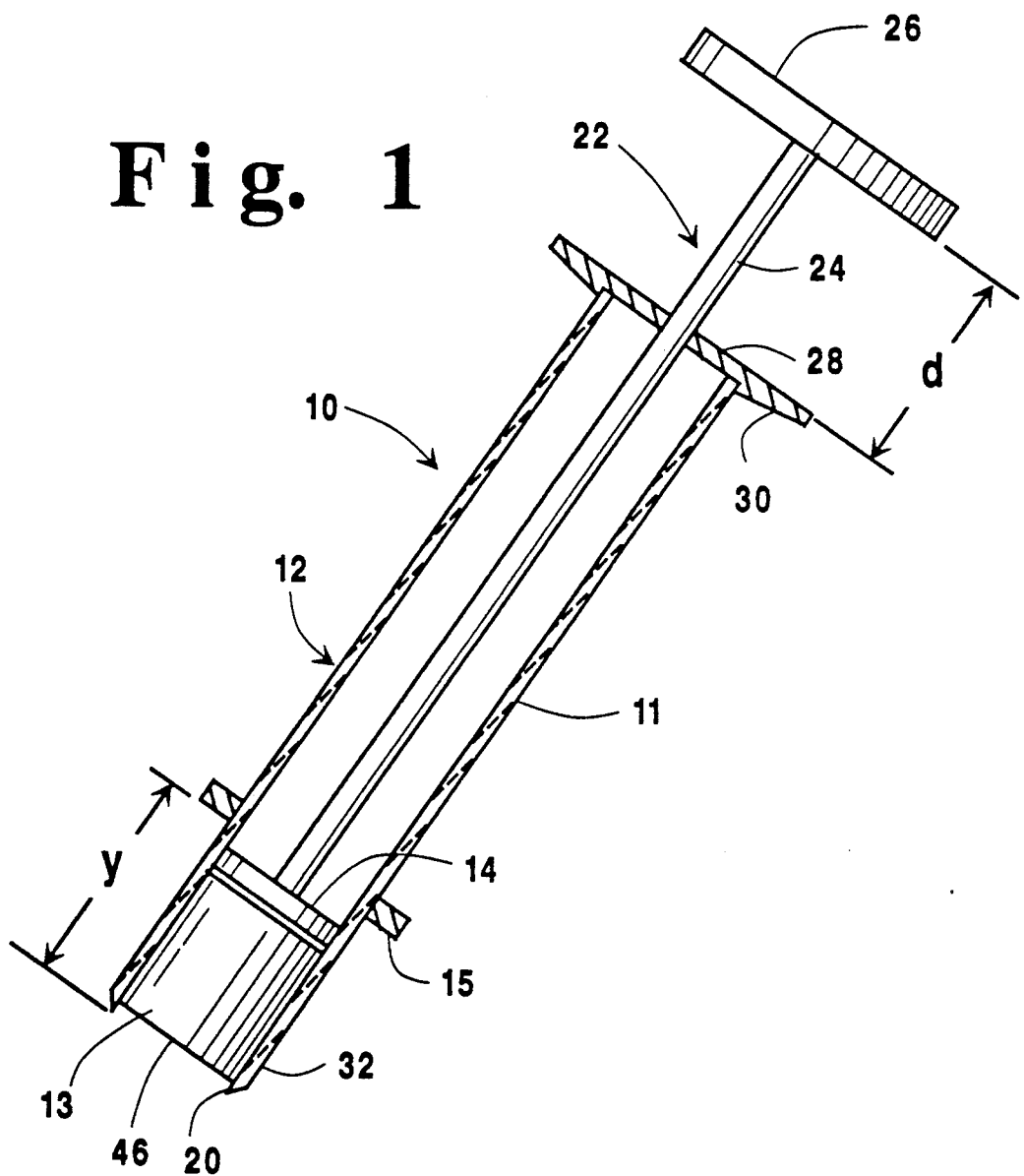
FIG. 1 is the longitudinal cross-sectional view of one embodiment of the present invention showing a soft tissue closure system comprising an implant delivery means and an implant positioned therein.

Referring now to the figures wherein like reference characters refer to the same elements, FIG. 1 depicts a soft tissue closure system shown generally as 10 comprising an implant delivery means 12 and an implant member 13 disposed within delivery means 12. The primary function of delivery means 12 is to deliver implant member 13 at a desired site in situ to effect the filling and closure of a void in the soft tissue of a living being. In a preferred embodiment, the soft tissue closure system of the present invention is utilized to effect the closure of a puncture or other opening in a blood vessel, duct or lumen. However, closure system 10 may also be utilized for the treatment of wounds resulting from other voids created to soft tissue in a living being, typically surgeries. Such applications include the filling of voids after removal of malignant tumors, necrotic tissues, deep bullet wounds, knife stabbing, and the like. Voids created by plastic or cosmetic surgery, and the like, are also able to be filled using the closure system of the present invention. Still further, the closure system of the present invention may also be used to stop the bleeding and fill the voids in diagnostic applications, such as tissue biopsy where a biopsy needle or other biopsy device is utilized.

While the following description and the figures are directed to the closure of percutaneous punctures in arteries, it should be understood from the above discussion that the present invention has greater applicability than this preferred embodiment.

Delivery means 12 is made from any biocompatible material, such as stainless steel; synthetic polymeric materials, such as polyethylene, polypropylene, polyvinyl chloride, polystyrene, polytetrafluoroethylene, polyurethane, or the like; natural polymers, such as collagen, elastin, or the like; and other such biocompatible materials which are well known to those skilled in the art. Desirably, the delivery means is made from inexpensive, disposable materials, such that it is simply discarded after use. For ease of manufacture and disposability, synthetic polymers are preferred.

The delivery means shown in the figures comprises a tubular member 11 having an outlet 20 at its distal end and an ejector means 22 slidably mounted at the proximal end 28 of tubular member 11. The tubular member is an elongated body having a depth insertion guide 15, an insertable front portion 32, and flanged projection 30.

Insertable front portion 32 has a fixed length "y" which is selected dependent upon the particular soft tissue site that is being repaired and will generally vary from about 2 mm to about 50 mm. It is only this insertable front portion 32 of tubular member 11 which actually is inserted into the patient's skin. The depth of insertion is easily controlled by the depth insertion guide 15 which is positioned on tubular member 11 at the length "y" such that the tubular member cannot be inserted past this guide. Guide 15 may simply comprise a partial or full circumferential projection or ledge which will cause the insertion of the delivery means to stop once the insertable front portion has been inserted, said ledge then simply resting upon the outermost surface of the patient's skin. The shape or design of the guide is not critical as long as it is capable of controlling the depth of the insertion.

The insertable front portion 32 is preferably constructed of an outside diameter which is less than the introducer sheath that is used for a particular intraluminal procedure so as to enable the insertable front portion 32 to be easily inserted through the skin and be juxtaposed to the percutaneous puncture site. Depending upon the particular intraluminal procedure, the outside diameter may vary from about 1 mm to about 5 mm. Except for the insertable front portion 32, the rest of tubular member 11 may have any outside diameter inasmuch as it does not enter the repair site. Desirably, however, for each of construction, the entire tubular member is typically made having the same inside and outside diameters.

Flanged projection 30 is arranged to be grasped by the fingers of the user as the implant member 13 is ejected by ejector means 22. The flanged projection 30 may completely or partially circumscribe tubular body 11 at its proximal end 28.

The ejector means 22 comprises an elongated, cylindrical rod-like member 24 having a push plate 14 attached to its distal end being in a plane which is perpendicular to its longitudinal axis and a thumb rest 26 attached to its proximal end also being in a plane which is perpendicular to the longitudinal axis of rod-like member 24. Push plate 14 is disposed inside of tubular member 11, in insertable portion 32, and has an outside diameter which is slightly less than the inside diameter of insertable portion 32 to enable the push plate 14 to travel down the longitudinal axis of insertable portion 32, to push or force implant member 13 out of the outlet 20. Rod-like member 24 is able to be retracted to a distance of "d", as shown in FIG. 1, which distance is only slightly longer than the length of the implant member 13, so as to ensure complete release of the implant and, most importantly, not push the implant a distance beyond that which is desired. Thus by controlling the length "y" of insertable portion 32, the length of the implant member 13, and distance "d", the implant member 13 is precisely positioned at the repair site.

Figure 2:
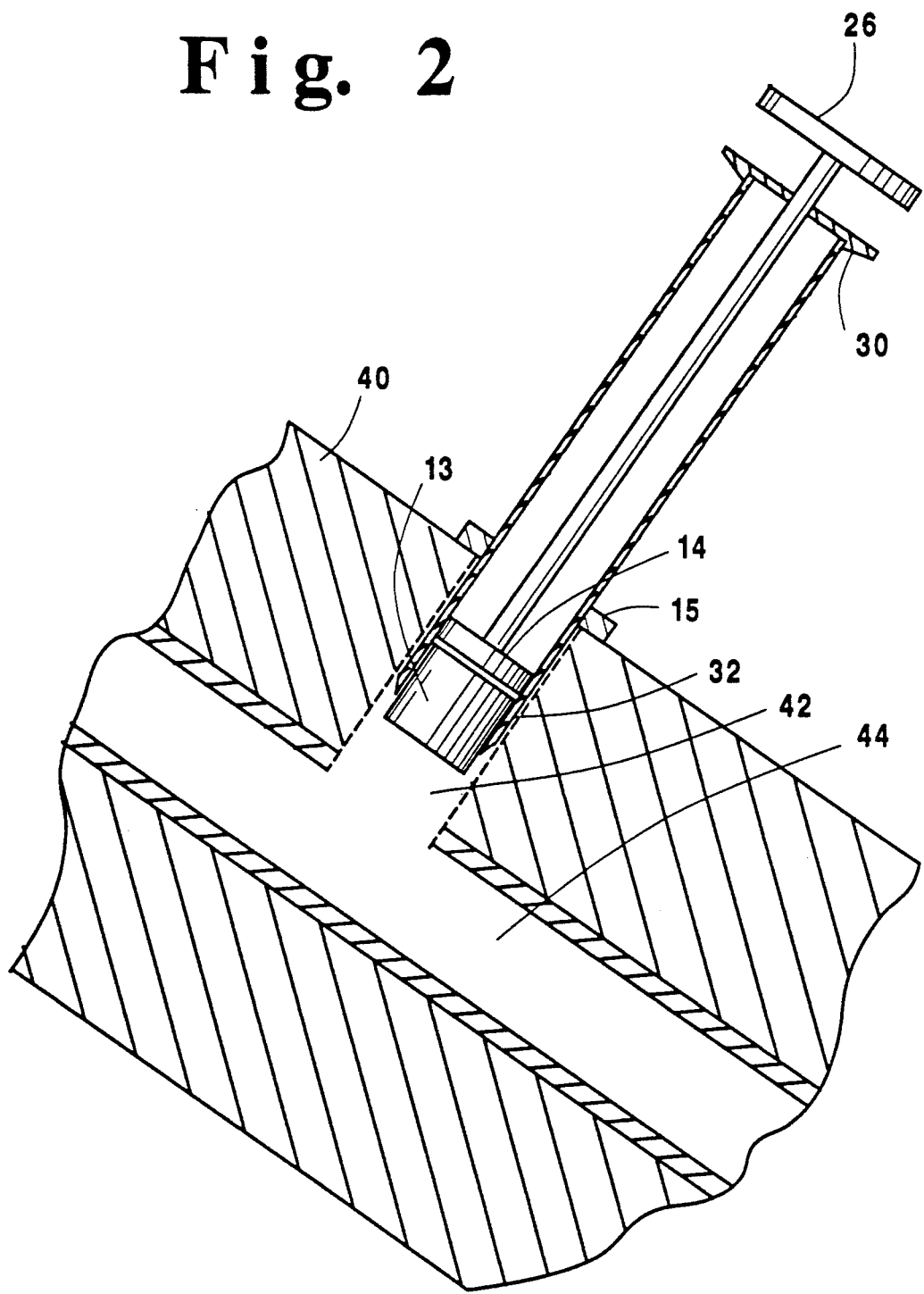
FIG. 2 depicts the use of the system at a percutaneous puncture site delivering the resorbable implant in cross-sectional view.

In use, the closure system of the present invention is desirably utilized as soon as possible after the removal of the introducer sheath from the puncture site. As shown in FIG. 2, insertable portion 32 is inserted at the repair site through the puncture 42 in skin 40. Depth insertion guide 15 controls the depth of insertion, stopping the travel of the insertable portion 32 once the guide rests upon skin 40. To effect the delivery of the implant member to the repair site, the user grasps projection 30 with his fingers and places his thumb on rest 26. By applying pressure to the thumb rest, the ejector means travels a distance "d" thereby ejecting implant member 13 and delivering it directly over the percutaneous puncture site 42 of vessel 44.

Figure 3:
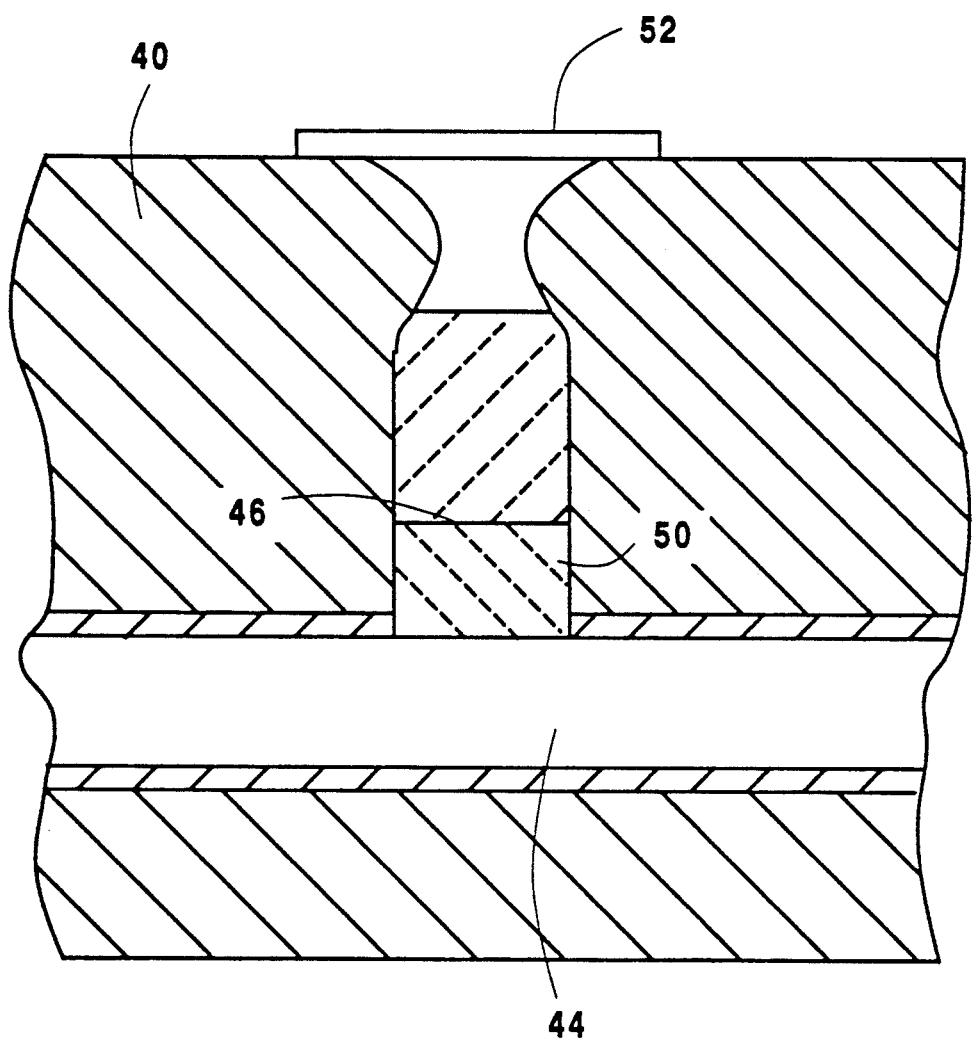
FIG. 3 depicts the resorbable implant in place in cross-section.

As more clearly shown in FIG. 3, implant member 13 is not positioned inside of the lumen of vessel 44, but rather, by the controlled insertion depth provided by the present invention, is delivered extravascularly such that end 46 of the implant member rest outside and directly on top of the punctured vessel. The ejected implant member 13 expands quickly in situ to completely close the puncture site as the delivery device is slowly being removed.

FIG. 3 is a schematic representation of a closed puncture site. The implant member 13 is shown as having considerably swelled and the blood around the implant member has been absorbed and clotted through a collagen induced hemostatic mechanism forming blood clot 50. A wound bandage is shown as 52.

The implantable, resorbable member 13 is made primarily from biopolymers, such as proteins, polysaccharides or the like. Preferably, a collagen based material is used due to its intrinsic hemostatic properties.

Type I to type XII collagens may be used either singularly or in combination for the manufacture of the implantable member 13. Preferably, type I collagen is used due to the availability of this material in large quantity, the ease of its isolation and purification, and proven hemostatic properties. The primary source of type I collagen is tendon, skin, bone, and ligament. Both human and animal tissues may be used to isolate the collagen. In general, animal tissues are preferred due to easy availability in fresh forms from local slaughter houses.

In preparing the implantable member 13, type I collagen is first isolated and purified. A review of the preparation of collagens can be found in "Methods in Enzymology vol. 82, pp. 33-64, 1982". In particular the collagen of the present invention may be prepared by the following method.

First, a native source of type I collagen, such as skin, tendon, ligament or bone is first cleaned of fat, fascia and other extraneous matter and washed. The clean and washed collagen containing material is then comminuted by slicing or grinding. Bone material is subsequently subjected to a demineralization procedure. This is achieved either with an acid solution such as hydrochloric acid or a solution of chelating agent such as ethylenediaminetetraacetic acid (EDTA).

The material is then subjected to a defatting treatment using fat solubilizing agents such as ethanol, propanols, ethers or a mixture of ether and alcohol. The defatted collagen containing material is then extracted in a neutral salt solution to remove neutral salt soluble material. Typically, 1M NaCl solution is used for this purpose. The high ionic strength salt solution weakens the non-specifically bound non-collagenous materials which are solubilized and removed. The salt extracted collagen containing material is then washed with deionized, distilled water.

The neutral salt extracted collagen containing material is then subjected to an acid extraction in the presence of a structure stabilizing salt to further remove acid soluble non-collagenous materials. Applicable acids include acetic acid, lactic acid, hydrochloric acid, sulfuric acid, phosphoric acid, and the like. Regardless of which acid is used, the pH of the acid solution is adjusted to be below 3. The salt used includes sodium chloride, ammonium sulfate, sodium sulfate, or the like. Acid extraction weakens the interaction between the collagen and the acidic non-collagenous impurities which are solubilized and removed.

The acid extracted collagen is then neutralized by adjusting the pH to its isoelectric point at pH of from about 6 to about 7 by adding a base. Applicable bases include sodium hydroxide, potassium hydroxide, ammonium hydroxide, and the like. By adding a base, the collagen coacervates. The coacervated collagen is then filtered by means well known in the art such as using a stainless steel mesh filter under vacuum.

The acid extracted, base neutralized collagen is then washed with deionized, distilled water to remove the residual salt formed by the neutralization procedure. The washed collagen is then subjected to a base extraction in the presence of a structure stabilizing salt. Such bases are well known in the art such as sodium hydroxide, potassium hydroxide, calcium hydroxide and the like. Regardless of which base is used, the pH of the solution is adjusted to be above 13. Base extraction weakens the interaction between collagen and the basic non-collagenous impurities. By adding the base, non-collagenous materials are solubilized and removed. The base also lowers the isoelectric point due to a partial deamidation of glutamines and asparagines in collagen which produce additional carboxyl groups. The base extracted collagen is then coacervated by adjusting the pH to its isoelectric point at a pH of from about 4.5 to 5.5 by adding an acid to the collagen dispersion so as to fully separate the fibers from the solution for ease of filtration. Such acids include hydrochloric acid, sulfuric acid, acetic acid, lactic acid, phosphoric acid and the like. The coacervated collagen is then filtered. After discarding the extraction solution, the fibers are washed with deionized, distilled water to remove the residual salts resulting from neutralization of the extraction solutions. The thusly purified collagen is stored in a freezer or stored in freeze-dried form for the preparation of collagen implantable member 13.

To fabricate a collagen implantable member 13, a collagen dispersion is first prepared in a manner well known in the art. One such preparation is taught in U.S. Pat. No. 3,157,524, which is incorporated herein by reference as if set out in full. Another preparation of collagen dispersion is taught in U.S. Pat. No. 3,520,402 which is also incorporated as if set out in full.

In particular, the collagen dispersion of the present invention may be prepared by the following method.

The purified collagen material is first dispersed in $1 \times 10^{-4}$M NaOH solution to swell the collagen fibers. The collagen material is then homogenized by any conventional means such as with a blender or homogenizer so as to fully disperse the fibers. The homogenized collagen is then filtered to remove any unswollen aggregates by means well known in the art such as by passing the dispersion through a stainless steel mesh screen. The pH of the dispersion is adjusted to about 7.4 by adding 0.01M HCl. The initial dispersion in a base allows the neutralization step to be carried out without passing the isoelectric point so as to not cause coacervation of the collagen and obtain a more uniform dispersion at pH 7.4. The dispersion is then de aired by vacuum. The resulting collagen dispersion may then be used to prepare the self-expandable, implantable soft tissue closure device.

Typically, the weight percent of collagen in a dispersion is from about 0.5 to about 5.0, preferably in the range from about 1.0 to about 4.0. Higher weight percent of collagen than 5.0 in the dispersion can be obtained by centrifuging the dispersion in a centrifuge and discard the supernatent. Generally, the higher the centrifugal force applied to the dispersion, the higher the weight percent of collagen in the dispersion after removing the supernatent.

In one embodiment of the present invention, if the collagen soft tissue closure system is intended to function as a medicinal delivery vehicle, then in addition to the type I collagen, medicinal additives may optionally be included in the dispersion, such as antibiotics, thrombin, polysaccharides such as hyaluronic acid, chondroitin sulfates, alginic acids, chitosan and the like, growth factors such as epidermal growth factors, transforming growth factor beta (TGF-B) and the like, glycoproteins such as fibronectin, laminin, and the like, type II through type XII collagens, and mixtures thereof.

The collagen dispersion is then poured into molds. The shape of the mold may be cylindrical, rectangular, spherical or any other shape so long as the size of the mold is larger than the inner diameter of insertable front portion 32. For a 2 mm internal diameter (I.D.) insertable front portion 32, and a cylindrical implantable collagen member 13, the diameter of the mold is preferably in the range of from about 3 mm to about 15 mm and the height of the mold is from about 3 mm to about 15 mm.

The molds containing the dispersion are then placed in a freezer maintained at a temperature of from about $-10°$ C. to about $-50°$ C. for a length of time sufficient to freeze the water present in the dispersion, generally for about 1 to about 24 hours. The frozen dispersion is then subjected to freeze-drying so as to remove the frozen water. This freeze-drying procedure is carried out in a commercial freeze dryer, such as that manufactured by Virtis, Stokes or Hull, at conditions well known to those skilled in the art. Typically, the vacuum within the drying chamber is maintained at from about 50 um to about 300 um of Hg, at a temperature of from about $-10°$ C. to about $-50°$ C. for about 16 to about 96 hours. The temperature is then raised to about 25° C. for about 3 to 24 hours.

The freeze-dried, highly porous collagen matrix is then subjected to a crosslinking process to introduce additional intermolecular crosslinks to stabilize the form of the collagen matrix. The crosslinking is carried out by means well known in the art. Any reagents which can chemically react with amino groups, hydroxyl groups, guanidino groups, carboxyl groups that can link the side chains of different collagen molecules ma be used to crosslink the collagen matrix. This can be accomplished with chromium sulfate, formaldehyde, glutaraldehyde, carbodiimide, adipyl chloride, hexamethylene diisocyanate and the like. The rate of in vivo resorption of the collagen is dependent upon the degree of intermolecular crosslinking in the collagen matrix. Factors controlling the extent of crosslinking are the type and concentration of the crosslinking agent; the pH, time and the temperature of incubation in the liquid phase; or the vapor pressure of the crosslinking agent, time, temperature and the relative humidity when carrying out crosslinking in the vapor phase. Desirably, the collagen matrix of the present invention is crosslinked to the extent that the collagen is completely resorbed within about 2 to about 10 weeks.

Appropriate crosslinking of the freeze-dried matrix introduces several very important properties of the present invention for the specified medical application as a soft tissue closure device. Effective crosslinking locks in the physical geometry of the matrix which is defined by the shape of the mold. Consequently, the matrix behaves elastically when a stress is applied to the matrix. That is, when the matrix is deformed or compressed physically, it will return to its original form and size upon relaxation or release of the external stress. This elastic behavior of the appropriately crosslinked freeze-dried collagen matrix is especially manifested when the collagen matrix is in the wet state, as when it absorbs blood at the puncture site. This is a result of hydrophilicity and the Donnon osmotic pressure of the collagen matrix. The recovery time from the deformed or compressed state to the original shape in the wet state is as short as from about 1 second to about 30 seconds. Desirably, the recovery time is from about 3 to about 10 seconds.

Another important property caused by crosslinking the collagen matrix is its solution uptake capacity, or the blood absorption capacity, when utilized to seal the puncture site and induce hemostasis. The solution uptake of the crosslinked collagen matrix of the present invention is limited by the size of the mold which defines the total volume of the matrix of the present invention. The total volume of a matrix is defined by the geometry of the mold. Typically, when the mold is of the form of a cylinder, the volume is defined by the area of the base of the cylinder and the height of the cylinder. The desirable volume of the matrix when in use for puncture site closure is dependent upon the particular size of the introducer sheath used. Particularly, when a 9F (about 3 mm) introducer sheath is used, the desirable dimension of a cylindrical matrix is to have a base dimension of from about 4 mm to about 15 mm, and a height of from about 2 mm to about 10 mm.

Yet an additional property controlled by crosslinking the collagen matrix is its density. Dependent upon the particular puncture site to be repaired and the physical, chemical and biological requirements, the density of the matrix in the fully expanded configuration may vary from about 0.02 gram matrix material per cubic centimeter of the matrix volume to about 0.5 gram matrix per cubic centimeter matrix volume. Typically, to close a puncture sites from angioplasty procedures, the density of the matrix in the fully expanded configuration varies from about 0.02 gram matrix/cm$^3$ to about 0.15 gram matrix/cm$^3$.

The degree of crosslinking of the collagen matrix of the present invention can be measured by the hydrothermal shrinkage temperature ($T_s$) of the matrix, i.e. the onset temperature at which the matrix begins to shrink in its dimension in an aqueous environment as a result of the unwinding of the triple helical structure of the collagen molecules. The methods for measuring the shrinkage temperature of a material is well known in the art, such as by a differential scanning calorimeter, or by measuring the dimensional change using a cathetometer.

Generally, the degree of crosslinking is such that the shrinkage temperature of the collagen matrix is in the range of from about 50° C. to about 75° C., preferably from about 55° C. to about 65° C.

In one embodiment of the present invention, the collagen matrix is crosslinked with formaldehyde vapor. Either commercial formaldehyde vapor, or vapor of formaldehyde generated from a formaldehyde solution may be used. Particularly, the crosslinking is conducted in a chamber with a relative humidity in the range from about 80% to about 100%, preferably in the range from about 85% to about 95%, and in the presence of an excess amount of formaldehyde vapor, at a temperature of about 25° C. for a period from about 30 minutes to about 8 hours. Specifically, crosslinking by formaldehyde vapor generated from 1% formaldehyde solution at 25° C. and at 95% humidity for 60 minutes produces a collagen matrix of a shrinkage temperature of from about 55° C. to about 65° C. for a matrix of density from about 0.02 g/cm$^3$ to about 0.15 g/cm$^3$ in the fully expanded configuration.

The crosslinked collagen matrix is then subjected to a water mist treatment. Any commercial water mist sprayer is suitable for this purpose. The collagen matrices are sprayed for about 10 seconds to about 60 seconds while the collagen matrices are being tumbled in a container at about 25° C. The water mist treated matrices are then equilibrated in a closed container for about 30 minutes to further soften the matrices for the compression step which follows. As a result of this water treatment, the collagen matrices have a water uptake of about 10 to 40% by weight, based on the weight of the dry material. The water mist treated collagen matrix is then subjected to mechanical compression to reduce its size in order to fit into insertable portion 32. Particularly, when the matrix is in a cylindrical form, the mechanical compression is applied in the radial direction such that the base area is reduced to approximately the size of the I.D. of insertable portion 32. Generally, the compressed collagen matrix has a volume of from about 1/100 to ⅓ of the non-compressed matrix. The compressed collagen implantable member 13 is then inserted into insertable front portion 32. At this point, the loaded soft tissue closure system is individually packaged for sterilization.

The crosslinking of the matrix, the water mist treatment and the mechanical compression are important aspects of the present invention. More importantly, the sequence of operation as described in this invention is critical in providing the desirable properties of the collagen matrix. The density, the pore structure and the extent of swelling of the compressed collagen implant member is directly related to how the collagen matrix material was made. For example, a change of the order from the present invention to water mist treatment, mechanical compression and then crosslinking the matrix will result in a matrix which will not self-expand when the stress is released and which does not have the blood absorption capability.

While only the sealing of a percutaneous puncture seal has been discussed as an example to describe the present invention, it will be understood that various changes, modifications, and applications may be made without departing from the scope and the spirit of the present invention.

The above and other objectives, advantages and features of the present invention will be better understood from the following examples.

EXAMPLE 1

Preparation of the Collagen Dispersion

The fat and fascia of the bovine flexor tendon are carefully cleaned and removed and washed with water. The cleaned tendon is frozen and diminuted by slicing into 0.5 mm slices with a meat slicer. The tendon is first defatted with isopropanol (tendon:isopropanol = 1:5 v:v) for 8 hours at 25° C. under constant agitation. The extraction solution is discarded and equal volume of isopropanol is added and the tendon slices is extracted overnight at 25° C. under agitation. The tendon is then extensively washed with deionized, distilled water to remove the residual isopropanol. The defatted tendon is then extracted with 10 volumes of 1M NaCl for 24 hours at 4° C. under agitation. The salt extracted tendon is washed with deionized, distilled water. The fibers are next extracted with 10 volumes of 0.6M NaOH for 24 hours at 25° C. in the presence of 1M Na$_2$SO$_4$ under constant agitation. The alkaline extracted collagen is then collected by filtration and neutralized with 0.1M HCl and the fibers collected, washed to remove the residual salt and frozen.

An aliquot of the above purified fibers is first suspended in $1 \times 10^{-4}$M NaOH solution. The amount of fibers and base solution used is such that a 1.5% (w/v) of collagen suspension is reached. The swollen fibers are then homogenized in a stainless steel blender for 60 seconds. The thusly dispersed collagen material is filtered through a 40 um stainless steel mesh. The pH of the dispersion is then adjusted to about 7.4 by adding 0.01M HCl. The dispersed material is then de-aired by vacuum and stored at 4° C. until use.

EXAMPLE 2

Preparation of collagen Soft Tissue Closure Implant

Collagen dispersion prepared from Example 1 is poured into stainless steel molds of 10 mm in diameter and 5 mm in height. The collagen containing molds are then subjected to a freeze-drying procedure using a Virtis commercial freeze dryer. The conditions for freeze-drying are: freeze at −40° C. for 6 hours; drying at 150 um Hg at −10° C. for 24 hours followed by drying at 25° C. for 8 hours. The freeze-dried collagen matrices are then subjected to a formaldehyde vapor crosslinking in a crosslinking chamber containing excess amount of formaldehyde vapor (generated by a 1% formaldehyde solution at 25° C.), 95% relative humidity at 25° C. for 60 minutes. The crosslinked collagen matrices are sprayed with water mist for 10 seconds and equilibrated in a closed container for an additional 30 minutes. The water mist treated matrices are then compressed by rotating between two glass plates with a gap of 2.5 mm such that the diameter of the 10 mm sponge matrix reduces to about 2.5 mm. The compressed collagen matrix is then inserted into a prefabricated implant delivery means of 2.5 mm I.D. and 3.0 mm O.D. (member 11, FIG. 1).

EXAMPLE 3

Preparation of collagen soft Tissue Closure Implant in the presence of thrombin

The collagen dispersion from Example 1 is mixed uniformly with thrombin (collagen:thrombin = 10:1 w/w). The thoroughly mixed collagen/thrombin gel is then poured into the stainless steel molds as in Example 2. The subsequent steps are identical to the Example 2.

EXAMPLE 4

Characterization of Collagen Soft Tissue Closure Implant a) Density (g/cm$^3$)

The apparent density of the soft tissue closure implant in the fully expanded configuration is determined by first weighing the collagen matrix to obtain the dry weight. The volume of the matrix is then determined from the radius and the height of the sponge according to: $V = II \times r^2 \times h$, where r is the radius and h is the height of the matrix. The density of the collagen oft tissue closure implant of the present invention is in the range of from about 0.02 g/cm$^3$ to about 0.5 g/cm$^3$.

b) Swelling (g/g)

The swelling is measured by the amount of solution uptake per unit weight of the soft tissue closure device. The dry weight of the collagen matrix is first determined. The collagen matrix is next immersed in a buffered solution at pH 7.4 at 25° C. for 5 minutes. The wet weight is then determined. The swelling (g/g) of the collagen matrix is calculated as the difference of wet weight and dry weight of the matrix divided by the dry weight of the matrix. The swelling capacity of the collagen soft tissue closure implant of the present invention is in the range of from about 2 g/g to about 70 g/g.

c) Pore Size (um)

The pore size is obtained from the scanning electron microscopy of cross-sections of the collagen implant in its fully expanded configuration. The pore size of the collagen matrix of the present invention is in the range of from about 100 um to about 3000 um.

d) Relaxation Recovery Time (seconds)

The collagen soft tissue closure implant of the present invention in its compressed configuration is pushed out from the disposable delivery means into a buffered solution, pH 7.4 at 25° C. The compressed matrix is relaxed and hydrated and self expanded to the original fully expanded configuration. The time it takes to recover to the fully expanded configuration is recorded. The relaxation recovery time for the present invention is in the range of from about 1 second to about 30 seconds.

e) Shrinkage Temperature (°C.)

A 10 mg of the collagen matrix is first wetted in a buffered solution, pH 7.4. The sample is sealed into an aluminum sample pen and inserted into a sample holder of a differential scanning calorimeter. The buffer solution is used as a reference. The heating rate is 5° C./min. The shrinkage temperature is defined as the onset of the endothermic peak from the heat capacity versus temperature plot. The thermal shrinkage temperature of the collagen soft tissue closure implant of the present invention is in the range of from about 50° C. to about 75° C.

EXAMPLE 5

Method of Use of a Collagen Soft Tissue Closure Implant

An appropriately sized collagen soft tissue closure implant is inserted into a puncture site immediately after the introducer sheath is removed. The collagen implant is ejected into the puncture site and allowed to be fully hydrated and self-expanded in situ for 5 minutes. The disposable delivery means is then slowly withdrawn. Slight pressure is then applied to the wound for 5 to 10 minutes to ensure complete hemostasis and wound closure.

EXAMPLE 6

Method of Use to Close a Soft Tissue Site

An appropriately sized delivery means is inserted through a percutaneous site to the tissue site of interest. The collagen implant is then pushed out of the tubular delivery means via a piston to the tissue site while the delivery means is slowly being withdrawn. The collagen implant self expands to fill the voids of the soft tissue site.

The present invention may be embodied in other specific forms without departing from the spirit or essential characteristics thereof. The present embodiments are therefore to be considered in all respects as illustrative and not restrictive, the scope of the invention being indicated by the appended claims rather than by the foregoing descriptions.

What is claimed is:

1. A device for sealing a void in a soft tissue of a living being which comprises:

a) an implant, having a length comprised of collagen material which is capable of being resorbed in the living being characterized by being in a compressed configuration and self-expandable when wetted to contain an expanded average pore size of from about 100 μm to about 3,000 μm, said implant having a relaxation recovery time of from about 1 second to about 30 seconds and having a volume in its compressed configuration state which i from about 1/100 to about ⅓ of the volume of its expanded state and is formed by the steps comprising:
  (i) forming an aqueous dispersion containing collagen;
  (ii) pouring the aqueous dispersion into molds;
  (iii) freeze drying the aqueous dispersion to form a collagen matrix;
  (iv) crosslinking the collagen matrix by treatment with crosslinking agent;
  (v) spraying the crosslinked collagen matrix with water mist; and then
  (vi) compressing the water mist treated collagen matrix;
b) a delivery means having an outlet at its distal end and a depth insertion guide, said delivery means being adapted to be inserted into the void to a depth which is controlled by the depth insertion guide, said implant being disposed within said delivery means; and
c) a retractable ejection means capable of ejecting the compressed implant out of the said outlet a controlled distance into the void of the soft tissue to form an expanded, hydrated matrix which conforms to seal the soft tissue void, wherein (i) the depth insertion guide, (ii) the length of the implant, and (iii) the retractable ejection mans, in combination, control the positioning of the implant within the void.

2. The device of claim 1, wherein the self expandable resorbable implant is formed of a biocompatible, bioresorbable material.

3. The device of claim 2, wherein the biocompatible bioresorbable material is type I collagen.

4. The device of claim 1, wherein the delivery means is a tubular member having a longitudinal axis and wherein the ejection means comprises a pusher member located within the tubular member and arranged to move down the longitudinal axis to force the implant out of the outlet.

5. The device of claim 4, wherein the delivery means is formed of a biocompatible material.

6. The device of claim 5, wherein the biocompatible material is a synthetic polymeric material.

7. The device of claim 5, wherein the biocompatible material is a metallic material.

8. The device of claim 1, wherein the implant self expands to comform to the tissue void when in contact with body fluid.

9. The device of claim 1, wherein the implant is of any geometrical shape.

10. The device of claim 1, wherein the depth insertion guide comprises a projection extending outwardly from the longitudinal axis of the delivery means, the distance between the projection and the outlet defining the depth of insertion of the delivery means.

11. The device of claim 1, wherein the implant has a density from about 0.02 g/cm$^3$ to about 0.50 g/cm$^3$ in the fully expanded configuration, a solution uptake capacity of from about 2 g/g to about 70 g/g, a shrinkage temperature from about 50° C. to about 75° C., and a relaxation recovery time from about 1 second to about 30 seconds.

12. The device of claim 1, wherein the resorbable implant further contains medicaments selected from the group consisting of antibiotics, growth factors, thrombin, glycosaminoglycans, prostaglandins, type II through type XII collagens, glycoproteins, fibronectin, laminin and mixtures thereof.

* * * * *